US006883724B2

(12) United States Patent
Adiga et al.

(10) Patent No.: US 6,883,724 B2
(45) Date of Patent: Apr. 26, 2005

(54) METHOD AND DEVICE FOR PRODUCTION, EXTRACTION AND DELIVERY OF MIST WITH ULTRAFINE DROPLETS

(75) Inventors: Kayyani C. Adiga, Macon, GA (US); Rajani Adiga, Macon, GA (US); Robert F. Hatcher, Jr., Macon, GA (US)

(73) Assignee: Nanomist Systems, LLC, Warner Robins, GA (US)

( * ) Notice: Subject to any disclaimer, the term of this patent is extended or adjusted under 35 U.S.C. 154(b) by 34 days.

(21) Appl. No.: 10/247,205

(22) Filed: Sep. 19, 2002

(65) Prior Publication Data

US 2003/0127535 A1 Jul. 10, 2003

Related U.S. Application Data

(60) Provisional application No. 60/365,870, filed on Mar. 20, 2002, and provisional application No. 60/323,399, filed on Sep. 19, 2001.

(51) Int. Cl.[7] .................................................. B05B 3/04
(52) U.S. Cl. ............................... 239/102.1; 239/102.2; 239/463; 239/468
(58) Field of Search .......................... 239/102.1, 102.2, 239/144, 463, 468

(56) References Cited

U.S. PATENT DOCUMENTS

| | | | |
|---|---|---|---|
| 3,808,056 A | * | 4/1974 | Pitcher et al. .............. 136/208 |
| 4,113,809 A | * | 9/1978 | Abair et al. .................. 261/81 |
| 4,345,718 A | | 8/1982 | Horvath |
| 4,608,282 A | | 8/1986 | Runge |
| 4,659,564 A | | 4/1987 | Cox et al. |
| 5,300,260 A | | 4/1994 | Keshet et al. |
| 5,485,828 A | * | 1/1996 | Hauser .................. 128/200.16 |
| 5,588,504 A | | 12/1996 | Spiegel et al. |
| 5,922,247 A | | 7/1999 | Shoham et al. |
| 6,247,525 B1 | * | 6/2001 | Smith et al. ........... 165/104.25 |
| 6,357,671 B1 | * | 3/2002 | Cewers .................... 239/102.2 |
| 6,676,034 B1 | * | 1/2004 | Tanaka et al. ........... 239/102.1 |

* cited by examiner

*Primary Examiner*—David A. Scherbel
*Assistant Examiner*—Thach H. Bui
(74) *Attorney, Agent, or Firm*—Brian D. Bellamy (57) ABSTRACT

The present invention provides a method and device for production, extraction and delivery of an aerosol mist with ultrafine droplets. A high frequency wave generating device or other process generates very small particles or droplets from a reservoir of liquid or material to be atomized. A helical flow of a carrier gas medium such as air is directed into a container and creates a high throughput aerosol of air and fine droplets. The aerosol is delivered through a suitable outlet such as by deflecting the aerosol upwards and providing a tube centrally situated with respect to the helical flow such that the aerosol will discharge through the tube in high quantity of throughput and high quality of stable aerosol of very fine mist droplets. The methods described utilize in-situ extraction of fine mist droplets using helical flow behavior as opposed to forced convection ejection of mist or inertial separation of droplets by separators.

40 Claims, 6 Drawing Sheets

METHOD AND DEVICE FOR PRODUCTION, EXTRACTION AND DELIVERY OF MIST WITH ULTRAFINE DROPLETS

PRIORITY CLAIM

The present application claims priority of U.S. provisional patent application No. 60/365,870 filed on Mar. 20, 2002 and U.S. provisional patent application No. 60/323,399 filed on Sep. 19, 2001.

BACKGROUND OF THE INVENTION

1. Field of the Invention

The present invention relates to the creation, extraction and high throughput delivery of very fine mist for humidification, fire suppression, blast mitigation or other chemical applications. In particular, the invention pertains to generating a mist containing very fine droplets at ambient pressure from a reservoir of water or liquid, and, then, effectively aerosolizing very fine droplets from the mist using swirl or helical flow behavior for delivery with sufficiently high throughput for effective application.

2. Description of the Prior Art

Previously, ultrasonic transducer devices have been used in small-scale mist generation units to generate mists for familiar purposes such as medical inhalers and decorative fountains in indoor-outdoor applications. These small-scale mist generation units would produce from 5–10 ml/min of liquids. Due to demand for high throughput mist generators in recent years, significant improvement ensued in humidification applications by implementing systems with linearly arranged arrays of piezoelectric transducers to multiply the total throughput.

However, the mists generated from these prior high throughput units generally comprise both small and larger droplets, mostly greater than several microns in size due to the methods utilized in extraction and transport of the mist formed in the mist generating unit. For instance, existing high-throughput humidifier designs use a fan or fans to directly push the mist upwards out of the container from behind the transducers. In these designs where mist is driven out of the misting chamber by a fan, large droplets of mist fall back into the liquid reservoir. However, the direct air current impinging on the water fountain in these humidifiers further forces the mist coming out of the humidifier to contain large proportions of the more coarse water droplets found in the center of the mist fountain. These impinging airflow-based systems transport significant amount of moisture due to forced convection currents. Thus, the final mist still contains coarser droplets. Moreover, residence time of the mist and carrier in the misting chamber is too short and not favorable for stable aerosol formation.

U.S. Pat. Nos. 5,300,260 and 5,922,247 provide examples of current technology for existing high-throughput humidifier designs. U.S. Pat. No. 5,300,260 to Keshet et al. uses multiple transducer units arranged in a circular geometry to achieve higher throughput. In Keshet air is passed through a central tube, and the flow of air is deflected by a domed-shaped top-hat back into the mist chamber or reservoir. The air flow directly impinges on the misting region and picks up mist and carries upwards. No special separation device is implemented for separation of coarser mist droplets not large enough to fall back into the fountain. In another embodiment, air is passed through tubes surrounding individual transducers. This air carries the mist upwards. Again, the device has not means of achieving optimum aerosol formation or separation of coarser droplets, and airflow directly impinging from above on the mist formation region would negatively affect optimum aerosol formation and separation.

U.S. Pat. No. 5,922,247 to Shoham et al. uses multiple transducer arrays to achieve increased mist throughput and the use of a high velocity air stream to first push the mist from the production chamber to a common chamber. Shoham briefly mentions the post-processing of the mist driven out of the misting chamber by forced convection using high velocity air and then again using high velocity air to produce a cyclone action and using inertial separation to separate larger droplets. The high velocity jet of air impinging on the sides of the conical chamber would collapse or vaporize mist droplets, and the high-speed inertial separation would cause vaporization or condensation surface shearing action. Thus, the transport and post-processing of the mist would cause significant loss of mist by coalescence and condensation into liquids.

As a result, these mists created by prior mist generators include many shortcomings that are disadvantageous for humidification and other applications. Additionally, maximum throughput reportedly generated by prior methods of has been limited to about 0.25 liter per minute (Lpm) and uses generating apparatus of unacceptably large physical size and high cost.

The shortcomings of mist droplets greater than several microns (referred to herein as large droplets) include that the droplets collapse easily due to coalescence and drop out to form liquids without reaching their intended target point or spaces. These large droplets are obstructed by physical objects and condense and drop out and, thus, do not display gas-like flow behavior, which causes crack and crevices and other areas to remain unaffected by the mist. Dropping out and condensation causes the amount of liquid needed in applications to be very high, which also leads to leaving the areas treated damp because of deposited liquid causing collateral damage in the area treated.

In specific applications such as humidification, fire suppression and blast mitigation, fast vaporization of extremely small droplets is an important property for providing an efficient cooling process. In recent studies, the inventors have observed that in sub-micron diameter droplets reaching nanometer scale the molecules in each droplet tend to migrate towards the surface of the droplet making the droplet very reactive for several applications. Thus, the need has been discovered for efficient aerosol formation, extraction, separation and delivery of mist from the mist fountain chamber, whereby the delivered mist is formed of extremely small droplets.

SUMMARY OF THE INVENTION

The invention provides a method and apparatus for producing, aerosolizing and delivering a mist comprised of a large portion of very fine droplets of about one to five micron or less. Advantages are provided by the invention in the generation of very stable mists comprised of mostly fine-scale sub-micron diameter mist droplets, as well as in the generation of mists comprised of a variety of mist droplets of larger scale, while providing for advantages in efficiency and throughput. The mist is generated at ambient pressure using electric ultrasonic transducers to convert electrical frequency input into mechanical ultrasonic vibrations. The mist throughput is scalable using variations of frequency and oscillator surface area, and using a multiple channel system of transducers. Delivery devices may be designed for application by hand to small areas, to medium scale applications suitable for device designed to be carried by backpack, or for large scale applications delivered to entire rooms or buildings.

The quality of the mist is maintained by using sufficient frequency and conditions to produce a plume of mist having a high number of very small sub-micron to only several micron scale droplets concentrated about the exterior portions of the plume. The invention provides for primarily extremely small droplets to be extracted from the plume using a smooth helical or swirling flow of carrier gas in each plane beginning at the surface of the liquid where droplets are formed. The gentle swirling airflow assists in the in-situ extraction or picking-up of fine mist from the generation chamber and formation of an aerosol mist that is very stable. The in-situ extraction of fine mist differs uniquely from inertial separation by passing the mist into a separate chamber.

In this case the swirling flow creates relatively weak axial (vertical component velocity) velocity while maintaining adequate circumferential or tangential component velocity. Thus, the flow of carrier gas generally creates a helical wave-like velocity as shown in the figures. The preferred carrier flow does not distort the capillary wave production of droplets, which is generally accompanied by 1–6 inch high spouts ejecting large fountain droplets.

The carrier gas is applied tangential to the extraction column so as the swirling flow lifts or entrains only the smaller droplets without significantly disrupting the central portion of the fountain column. The larger droplets of the fountain are left in the center of the plume to fall back into the reservoir of solutions as a fountain of liquid or water. The fountain operates more efficiently in the production of very small droplets because of the minimized disturbance of the central portion of the fountain, and the smooth swirling flow lifts, reflects, or carries the fine mist slowly to a suitably situated outlet. In one embodiment, the fine mist is slowly lifted upwards in a helical waveform and output through an outlet located at the top of the container.

The entrained smaller droplets may be considered aerosolized, wherein sufficient residence time is provided for the mist of fine droplets to become very stable prior to discharge and delivery. Aerosol formation, extraction and application of droplets in the size range of 0.05 micron to 10 micron has been found very effective in applications such as humidification, fire suppression, blast mitigation, sterilization and sanitation.

Various configurations of the device may be provided for accomplishing the objectives of the invention. The mechanism of formation of swirl flow inside the mist-generating chamber, resulting in helical flow structure, may be accomplished by other means without using a tangential inlet for introducing such flow. Swirl generators based on multiple vanes and commercially available swirl or vortex generators can be utilized to create such flows and introduce such flows to the mist-generating chamber.

With respect to the outlet for the aerosol mist, various configurations may be suitable. For instance, an outlet may be oriented tangentially to the fountain column on the upper or lower portions of the container. Alternatively, an outlet could be situated at the top of the extractor container, or a vortex finder tube could be centrally located in the mist-generating container for upward discharge of the fine aerosol mist. Further, the outlet could be connected to a member of conically converging diameter to assist in concentrating the aerosolized mist for delivery.

In other examples of alternative configurations, multiple inlets tangentially situated to the fountain column could be provided to improve carrier gas flow, or multiple outlets could be provided for improved mist ejection. Additionally, arrangements may be provided that use multiple atomizers or transducers to improve function or throughput.

DETAILED DESCRIPTION OF THE INVENTION

The present invention and its various embodiments are described in terms of mist generation or droplet formation using an array of transducers, uniquely defined configuration of airflow into the mist generating location, aerosol formation, stability of mist, transport of aerosol, classification of mist, and configuration of mist outflow.

In a first embodiment, the present invention provides one or more piezoelectric transducers 10 connected to a power supply 12, usually an external driver. The piezoelectric transducers generate a mist from a liquid contained in a reservoir 14 at the base 16 of the unit. The reservoir and liquid may suitably remain at ambient pressure and at ambient temperature. Usually, the transducers are submerged in the liquid in the reservoir with the crystal submerged about 1–2 inches below the liquid surface or otherwise arranged in physical communication with the solution. The reservoir is contained within the chamber walls 18 of the device, and the walls are preferably cylindrical as depicted in FIGS. 2a, 2b, 3a and 3b. A typical misting chamber 20 will be about 2–3 feet high and about 1–2 feet in diameter. The scale and dimensions will vary widely depending on the scale of mist production unit.

The mist generation unit 20 may include an ingress inlet 22 and egress outlet 24 to provide liquid to create the reservoir 14. In some applications, a sensor 26 may be provided as shown in this transducer section of the mist generation unit to monitor the level of the reservoir, and a system may be provided for controlling the inlet and outlet of the reservoir to adjust the level accordingly.

Rather than utilizing high-pressure systems or heat-based systems, the present invention provides for production of sufficiently high throughput of quality fine mist using a high frequency ultrasonic device. Heretofore, using high frequency ultrasonic devices has been considered not practical for the throughput levels desired (1 to several liter per minute) of such a fine scale mist. Because the very fine mist droplets created by the invention are created at ambient pressure, no expensive technology is required to handle high pressure or heat so that the mist may be created cost effectively.

In the discussed embodiment, the liquid provided in the reservoir 14 is subjected to ultrasonic waves driven by the piezoelectric transducer 10 or other ultrasonic wave-generating device. The transducer provides the ultrasonic waves that atomize the liquid to produce mist droplets, by converting an electrical frequency to mechanical vibrations. The mechanical vibrations of the piezoelectric device facilitate atomization of fluids by producing ultrasonic pressure or sound waves with rarefaction and compression cycles. The ultrasonic waves produce surface capillary waves because of free surface oscillations where air and liquid interface. Beyond certain amplitude, the capillary waves elongate at the crests and produce atomized droplets. Extremely small droplets break out from the crests against surface tension. This capillary wave action is strongly supported as the applicable theory of mist droplet formation. However, in at least some cases, rarefaction produces cavitations in the liquid resulting in bubbles, which expand during the negative pressure excursion and implode violently during the positive excursion. These cavitations cause the imploding bubbles to surface out as small droplets during compression to form a fog-like mist. Regardless of the capillary wave action or production of cavitations, the ultrasonic waves produced by the high frequency vibration cause atomization of the liquid into a cloud of particles or mist droplets 28. The droplet size produced by the atomization process will depend on the cube root of surface tension of the solution, the density of the liquid, and the square of frequency of oscillation. Hence, the surface tension of the liquid is important in controlling the droplet diameter created by atomization and may affect the design of the ultrasonic device used in generating the mist plume. The equation to predict the droplet size in ultrasonic wave assisted atomization is given by the equation:

$$d = 0.34(8\pi\tau/\rho f^2)^{1/3}$$

where $\tau$ = the surface tension of the liquid
 $\rho$ = the density of the liquid
 $f$ = the exciting frequency of the transducer
 $d$ = the diameter of the droplet The droplets formed in ultrasonic wave generated mists show a relatively narrow distribution of size unlike in pressure-atomized droplets. For instance, generally with piezo transducers of 1–5 MHz, one can achieve a narrow range of 1–5 micron diameter droplets. One could also achieve a narrow range of sub-micron droplets using piezo transducers of appropriate frequency and configuration. If proper aerosolization of the droplets is achieved, the mist will be stable. However, if nucleation starts without proper aerosolization, the droplets will coalesce and finally condense into liquid. Typical transducers available commercially are used in medical applications, cleaning and humidifying. The known transducers operate with oscillating frequencies of 1.7 MHz to 2.4 MHz and produce 1 to 10 micron droplets of water mist. Modifications in frequency or the mechanics of the piezoelectric transducer may be made in accordance with the desires of the present invention for smaller droplet size, depending on the desired mist quality and quantity of small nanoscale droplets. A transducer may be varied in size of oscillating element to modify mist generation from the reservoir. Also, a transducer may accommodate frequency of mechanical oscillation of 20 MHz or more. And further, an array of piezoelectric oscillating elements may be arranged in combination to collectively form the atomizing element 10 and provide an additional means of increasing the atomization and generation of mist. For instance, in one embodiment an array of 9 piezoelectric elements may be arranged in a 3 by 3 array. The number of elements may vary depending on the throughput desired. For example, if each element produces 20 ml/min, then 50 elements would be needed to generate 1 liter per minute. Increased mist generation volume may assist in the throughput of fine quality droplets. However, it should be noted that increased throughput of a fine scale mist as discussed herein would not be possible without further improvements as provided by the invention for aerosolization, extraction and delivery of the mist droplets. As the number of transducer elements is increased in a given area and are closely packed for compactness of equipment size, the efficiency of air mixing with the droplets decreases and aerosol formation becomes inefficient. Finally, the throughput of the mist generator is reduced and ineffective. Therefore, a special carrier gas flow field implementation is the key to success in large-scale mist generation.

The reported method of extraction and delivery of mist is not only applicable to mist produced by ultrasonic device, but equally applicable to any mist or small particles produced by other methods. Other possible production means include laser light focused on a liquid surface and small particles (including sub-micron sized particles) generated by chemical or physical means. Therefore, it can readily be seen that the invention may be used in combination with such droplets or particles produced by other means.

Figures 1, 2A, 2B:
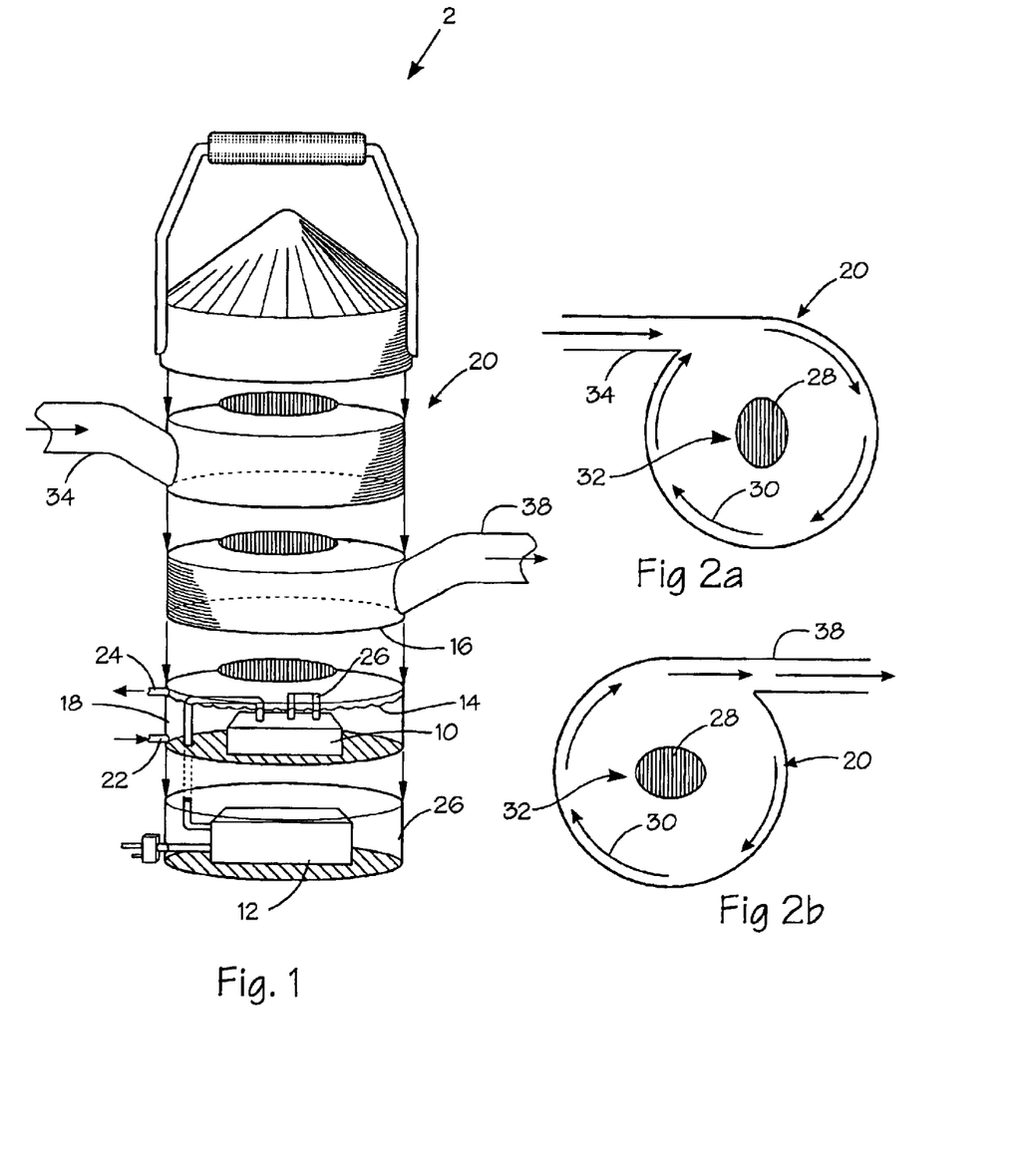
FIG. 1 is a schematic elevation view of an exemplary water mist generator in accordance with the invention.
FIG. 2a is a schematic top view of flow velocity vectors at the carrier medium ingress plane.
FIG. 2b is a schematic top view of flow velocity vectors at the carrier medium egress plane.
Figure 4:
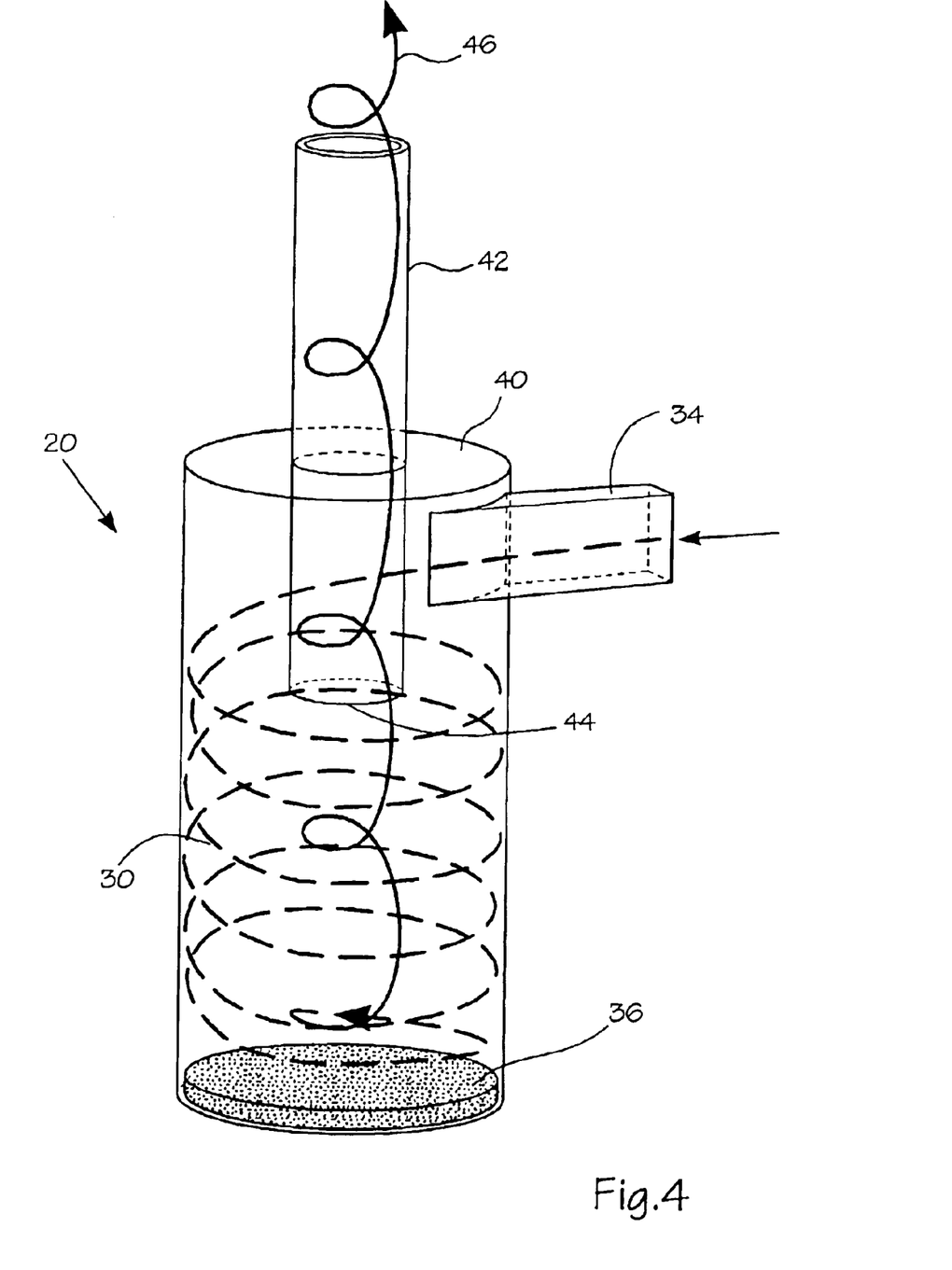
FIG. 4 is a perspective view of one embodiment of a device in accordance with the invention for generating and delivering a fine mist using helical downward flow of carrier gas and central outflow of mist.

The extraction method herein provides a device, as illustrated in the embodiment in FIG. 1, for delivering of mist containing very fine droplets of various scales from microns diameter to less than one micron in diameter. The mist is delivered in high quantity and quality. The extraction method operates by removing the smaller droplets from the plume or column 28 of mist being generated by the high frequency ultrasonic oscillations. In particular, the smaller droplets are concentrated away from the center of the plume 28 as shown in FIG. 4, while conversely the larger droplets are concentrated in the center. The present extraction method and device does not significantly disrupt the center of the plume of mist as it is generated. Rather, a flow of carrier gas or air is provided flowing tangentially 30 with respect to the plume at the base 16 of a cylindrical chamber 20.

The tangential flow 30 is directed to the outer portion 32 of circumference of a circular cross section of the plume 28 as shown in FIGS. 2a and 2b, such that the flow 30 is directed tangentially at the mist fountain column at its entrance, as shown by the inlet 34, into the fountain column. In each plane within the misting chamber 20, the directed carrier gas creates a swirling flow with higher radial velocity towards the circumference or wall of the chamber. The general flow will be helical about the central axis of the cylinder 20. The radial velocity of the swirling carrier gas flow at the center is relatively lower and finite, and, in response to the helical flow, the static pressure at the centerline of the cylinder is relatively low as compared to the pressure at the sidewalls 18 of the container. The flow of slowly swirling gas at the surface 36 of the liquid provides an environment for aerosol formation and restricts the coagulation and coalescence of droplets and, thus, restricts formation of large droplets.

Figures 3A, 3B:
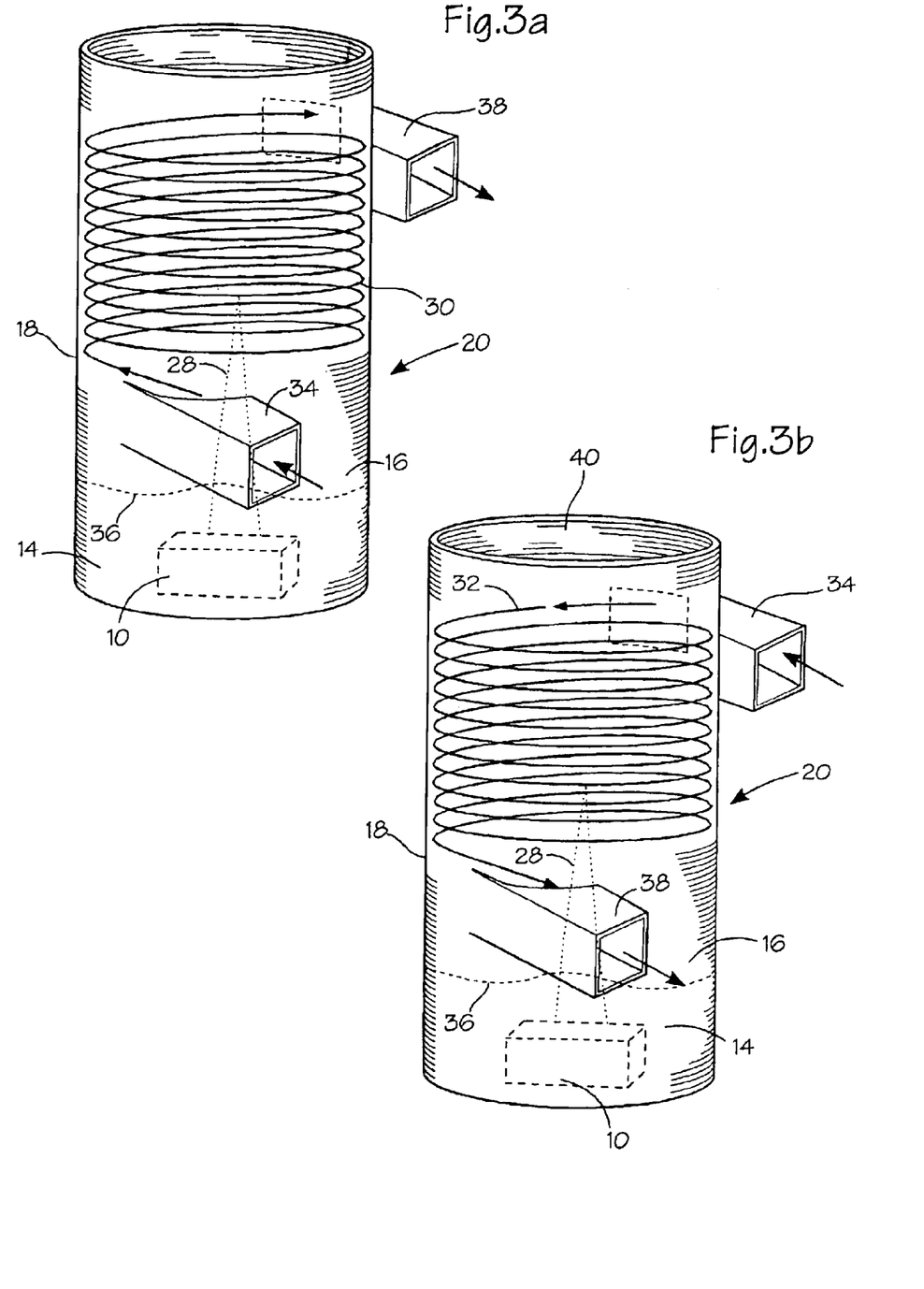
FIG. 3a is a perspective view of one embodiment of a device in accordance with the invention for generating and delivering a fine mist.
FIG. 3b is a perspective view of one embodiment of a device in accordance with the invention for generating and delivering a fine mist.

The outlet 38 and inlet 34 may be situated as shown in FIG. 3a with the inlet near the lower portion of the mist chamber 20. Alternatively, the arrangement may be switched as shown in FIG. 3b, and the inlet 34 may be situated near the upper portion of the chamber 20 with the outlet 34 preferably just above the level of the liquid reservoir 14. With the outlet near the surface level of the reservoir, the output of mist has been found to be more efficient in some configurations, possibly because mist in general is heavier than air.

An additional advantage of the invention is provided where multiple-component liquid mixtures are utilized as a source for the mist. In this case, the more volatile or low surface tension components may form droplets and escape in vertical columns. However, in a configuration as mentioned above, the helical path of the carrier gas will transport the more fine droplets of those more volatile components back to the liquid surface during entrainment and mixing of the mist.

Also, while the inlet 34 is preferably tangentially situated with respect to the chamber wall 18, the outlet 38 does not have to be tangentially situated to receive effective mist throughput. Alternatively, an outlet could be situated at the top 40 of the extractor container. Regardless of the alternate arrangement of inlet 34 and outlet 38, the accomplishment of an efficient throughput of a quality fine mist by generating a strong flow near the column walls 18 without disturbing the central plume 28 and entraining larger undesirable droplets does not change. The flow behavior created by the arrangement taught by the invention optimizes and improves the capillary wave and cavitations processes of creating fine mist droplets.

Providing cylindrical column walls 18 accommodates the desired tangential wallside flow shown in the figures. A rectangular geometry would not be as well suited without proper care and design to ensure the water fountain flow is not disturbed or impinged upon by the carrier gas medium.

Because the smaller droplets are situated in the outer portion 32 of the fountain 28, the tangential flow 30 of carrier gas operates as a filter or classifier to separate the smaller droplets from the plume and carry them to the outlet 38 of the device. The result of the tangential flow of carrier is a strong swirl of carrier gas flow along the sides of the device and near the outer wall of the chamber, but with very little flow of carrier gas in the center of the device or near the center of the chamber, which is illustrated in FIG. 3a. The smaller droplets in the mist near the outer portion 32 of the fountain 28 are pulled into the swirling flow along the wall 18 of the chamber, and the larger droplets closer to the center of fountain plume remain and fall back into the reservoir bed 14 of solution, as illustrated in FIGS. 3a and 3b. Thus, a mist having a high concentration of smaller droplets is produced that provides several advantages.

In the embodiment of FIG. 4, a tangential carrier gas inlet 34 is located at the top 40 of the misting chamber 20 or container. Within the container, a centrally located vortex finder tube 42 extends a desired length below the tangential inlet, and the vortex finder extends a desired length above the top of the container. The desired length of the vortex finder tube extending below the inlet inside the chamber is an important parameter and will vary depending on the mist generator scale and system configuration. Therefore, the extension length parameters of the vortex finder tube should be optimized accordingly. The tube 42 may be slanted slightly to avoid fountain droplets reaching directly into the inlet 44 of the tube. The entrance to the central tube may contain filters or twisted tubes to reduce the entry of any coarser droplets into the mist outflow. A downward swirling flow of carrier gas reaches the base 16 of the chamber following the helical spiral path 30 shown. As this carrier flow reaches the base of the unit, the carrier gas mixes with the mist droplets and forms an aerosol of extremely small water droplets. The downward flowing carrier gas reverses path after reflecting from the reservoir liquid surface 36 and carries the formed aerosol of mist 46 upwards to and through the centrally located vortex finder tube. Larger fountain drops and coarse droplets are left behind. For more narrow classification of droplets in the aerosol mist, the shape of the vortex finder tube may be configured conically and the geometry of the column 20 may be optimized. This embodiment provides excellent conditions for aerosol formation in terms of carrier flow pattern, residence time and amount of carrier and droplets.

Several fine mist generating devices 2 may be combined and connected to provide a series of chambers 20 to increase the overall mist throughput. Thereby, a given inlet mass flow of carrier gas may be provided to a first chamber, and successive chambers may receive mist flow from the preceding units. As additional fine mist droplets are gathered, the mist will proceed to an outlet or another successive unit. The chambers may be connected by conduits situated tangential to the chamber walls such that mist flow and carrier gas flow does not disturb the plume generated in each chamber. These devices may be modular and the number of devices to be in communication with each other may be varied at will.

In yet a further embodiment, additional swirl flow chambers (vertical or horizontally oriented) having tangential carrier gas flow inlets may be added at the outlet of the main mist chamber or container. These additional swirl flow chambers will take the expelled mist from the main misting chamber and further subject that mist to swirling flow to achieve further classification of droplets. Such post-processing may be desirable when a very narrow range of mist droplet size is required for a specific purpose. However, as mentioned beforehand, such post-processing will also decrease overall throughput due to coagulation, coalescence and vaporization of droplets.

Figures 5A, 5B:
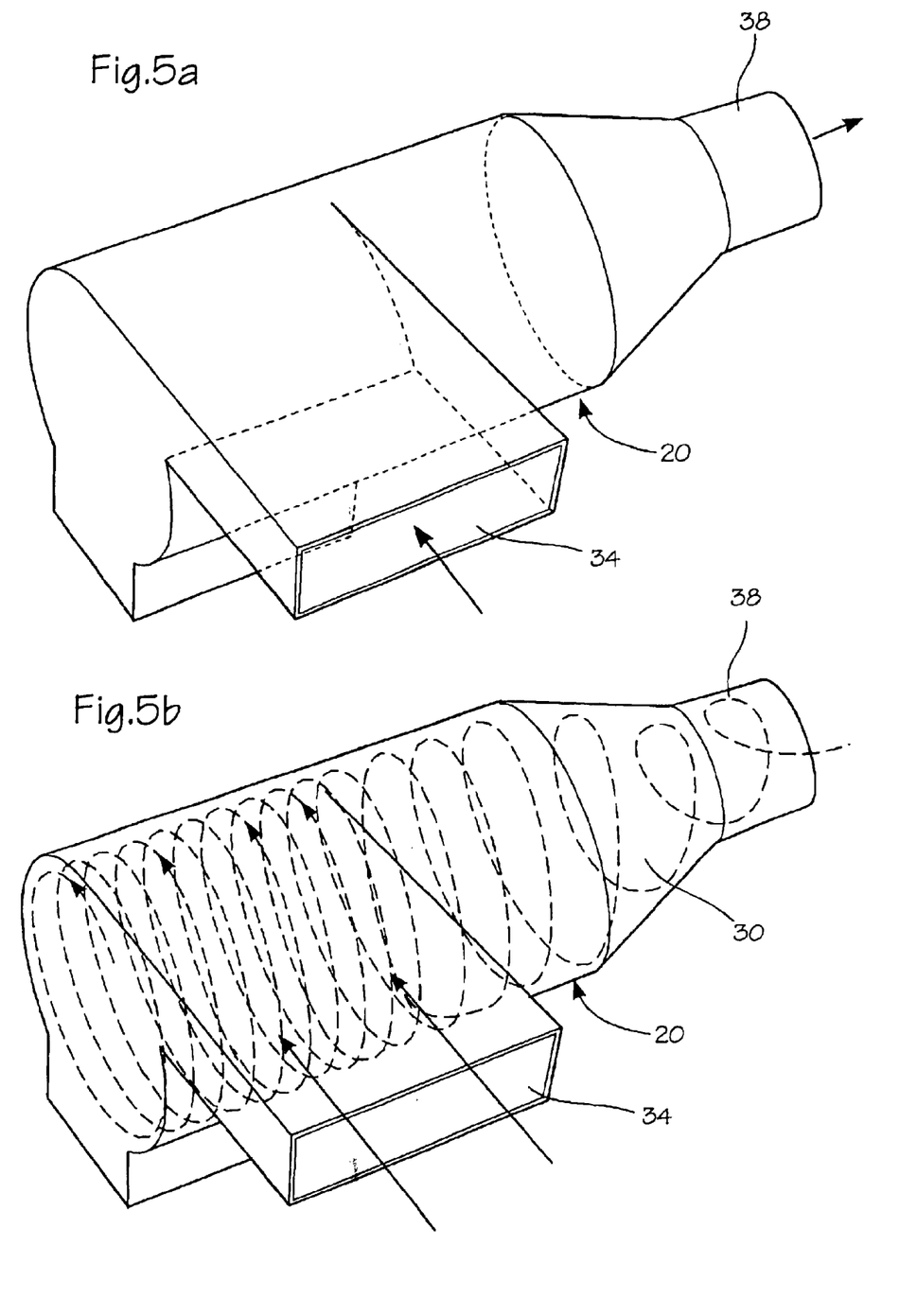
FIG. 5a is a perspective view of one embodiment of a device in accordance with the invention that is oriented for horizontal flow.
FIG. 5b is a perspective view of one embodiment of a device in accordance with the invention that is oriented for horizontal flow and depicts horizontal helical flow of carrier gas and mist.

Various other configurations of the device may be provided for accomplishing the objectives of the invention. As shown in FIGS. 5a and 5b, the cylindrical container 20 could be oriented horizontally and a tangential inlet 34 situated for creating a swirling flow 30 of carrier gas. In the horizontally oriented configuration shown, the carrier gas would flow horizontally as well and entrain fine droplets of mist. The helical path of the carrier flow is shown by line 30 in FIG. 5b. Similar to the other configurations herein, the swirl flow of carrier gas will provide adequate carrier and residence time to pick up the fine mist droplets, classify the droplets and provide effective aerosol formation of the mist. The mist is then delivered in a spiral flow as depicted. A horizontally oriented system may improve residence time of carrier and provide better mixing and aerosol formation. Further, because the extraction column is horizontal, larger droplets would be provided greater residence time during mixing to fall back into the base of the chamber by assistance of gravity.

Figures 6, 7:
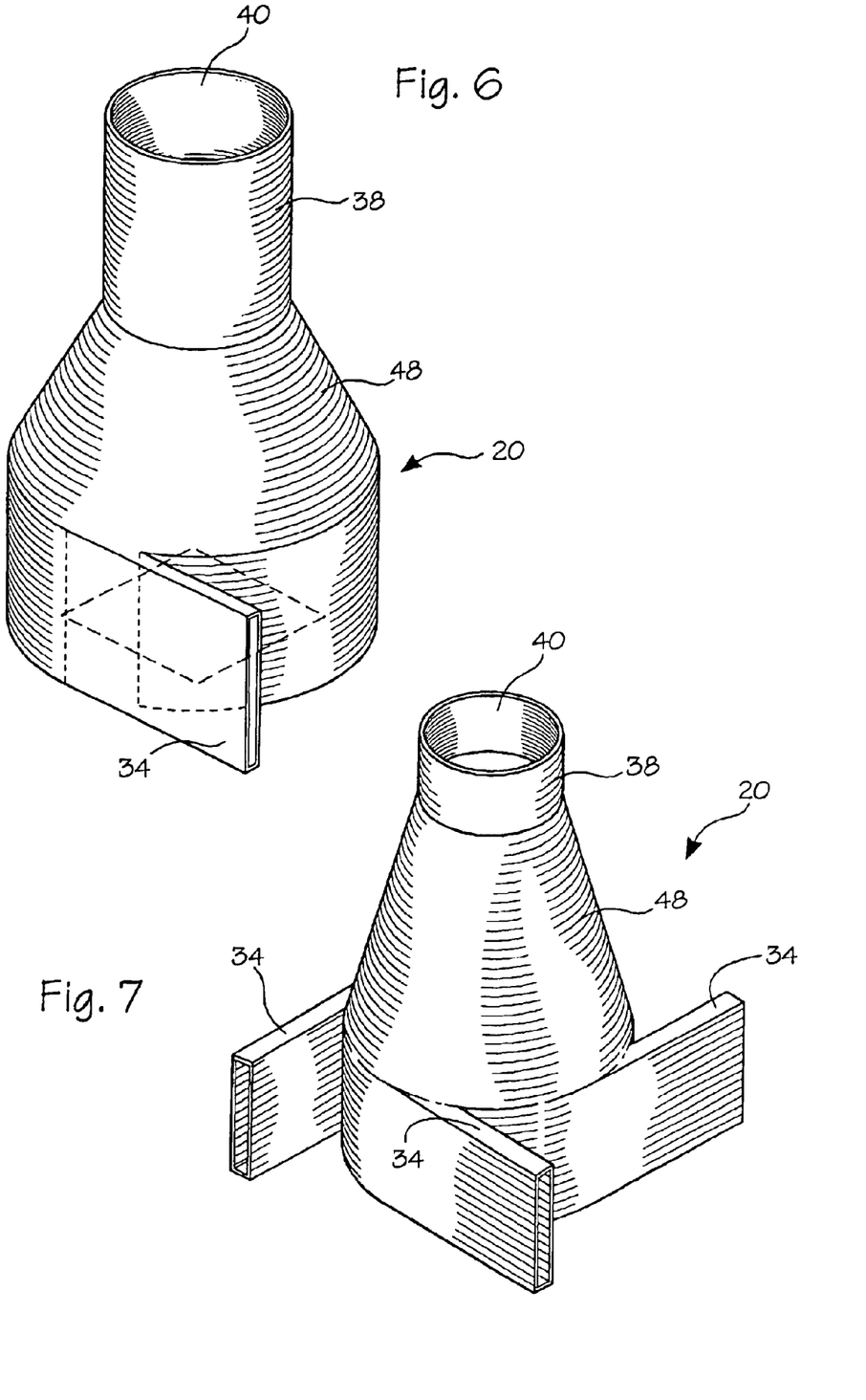
FIG. 6 is a front perspective view of one embodiment of a device in accordance with the invention having a conically converging portion connected to a mist outlet.
FIG. 7 is a front perspective view of one embodiment of a device in accordance with the invention having multiple tangentially situated inlets.
Figure 8:
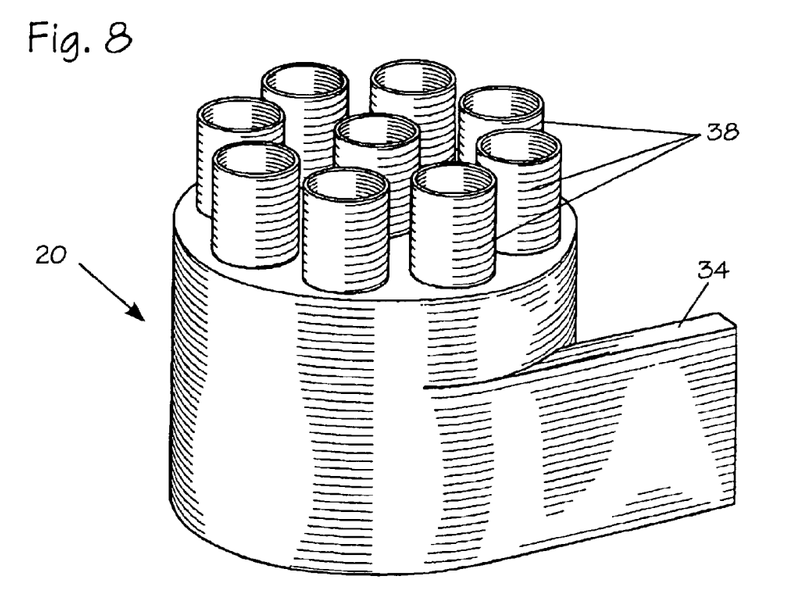
FIG. 8 is a front perspective view of one embodiment of a device in accordance with the invention having multiple outlets for mist ejection.

Yet other configurations are also contemplated as shown in FIG. 6, the outlet 38 could be connected to a conical portion 48 of the container 20 having a upwardly conically converging diameter to assist in concentrating the aerosolized mist for delivery. Also, as illustrated in FIGS. 7 and 8, multiple inlets 34 tangentially situated to the fountain column 28 could be provided to improve carrier gas flow, or multiple outlets 38 could be provided for improved mist emission.

Figure 9:
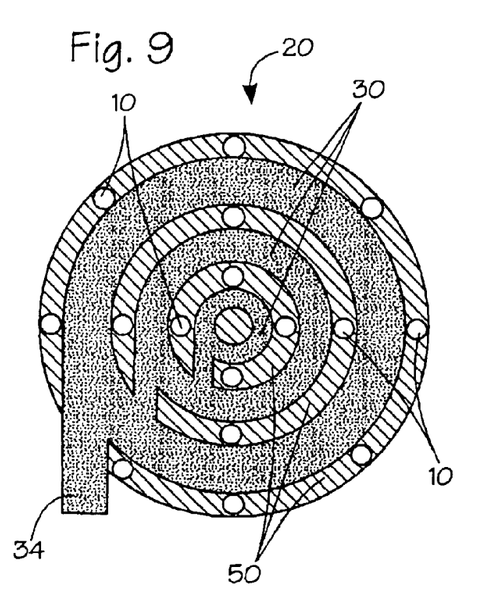
FIG. 9 is a schematic illustration of one embodiment of a device in accordance with the invention having several annular arranged atomizer elements, or transducer elements, and annular carrier medium flow pattern.

In more complex arrangements, multiple atomizers or transducer elements may be used to improve function or throughput. In FIG. 9 an annular array of atomizers 10 is shown. The container 20 is provided annular wall sections 50 for beneficial carrier medium flow 30 near the misting elements. The air or carrier medium enters tangentially between the circular arrays of transducers and flows to the center of the container to entrain and then emit an aerosolized mist of fine quality droplets.

Figure 10:
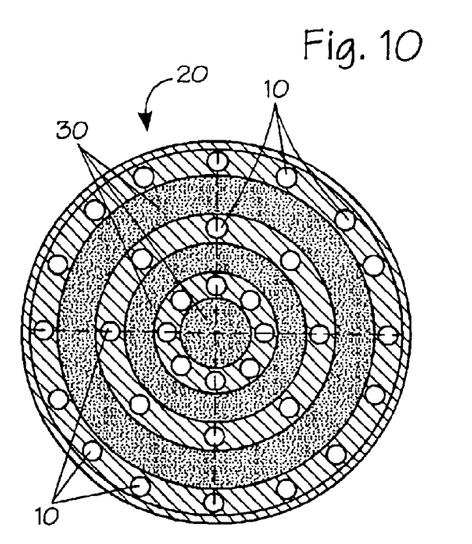
FIG. 10 is a schematic illustration of another embodiment of a device in accordance with the invention having several annular arranged transducer elements and carrier medium annular thereto.

In FIG. 10 several annular arrangements of misting transducer elements 10 are provided. Swirling carrier medium flow 30 is provided between the misting elements to entrain fine quality mist droplets and emit the aerosolized mist 46 from the container 20. The transducer elements may be arranged in troughs to further improve airflow and minimize disturbance of the central portions of the fountains.

In any case, the units may be modular and compact. For example, the units may be made compact by suitably arranging the transducers 10 in rectangular channels in rows and placing the swirl flow carrier gas chamber 20 on top. Further, a mist-generating unit may be made modular by adding more transducers to a base unit for generating atomized mist and adding a swirl flow unit on top of the transducer containing base. Such a configuration could be useful in developing units that are scalable according to desired throughput for the specific application.

The smaller droplets comprising the mist 46 will preferably be of less than one micron or nanoscale. A high quality mist comprised of droplets of 50–1000 nanometers (0.05–1.0 micron) or, alternatively up to 1–10 microns is made feasible by the generation, aerosolization and extraction methods discussed, and such mist may be produced by the present method at a throughput of up to 1 Lpm or more. The throughput of the device and methods described herein are variable from a few ml/min to a few liter/min, and, therefore, scalable to a variety of applications, whereby sufficient fine mist throughput is provided according to the scale needed.

Proper aerosol formation or aerosolization keeps the droplets stable in the carrier medium. Adequate air or other carrier medium must be provided adequate residence time without distorting the formation of capillary waves and droplet disintegration from the liquid surface. A directional sweep by a fan blowing air across the surface of the mist fountain adversely affects the fine mist generation rate and decreases throughput. Proper aerosol formation is also important when a large array of wave generating elements are present in a limited area for producing copious amount of mist, as droplets tend to coalesce and form liquid immediately when a carrier medium is not provided. The present invention achieves proper aerosol formation even in large-scale systems, such as 0.25 to 1 liter or more per minute, by providing aerosol formation immediately after droplets are ejected from the liquid surface.

The mist 46, when comprised of very fine droplets, characteristically performs as a pseudo gas-phase substance, as opposed to a liquid, vapor-phase, or gas-plasma substance, because the extremely small droplets exist in nearly molecular cluster state. Macroscopically the mist fluid looks like a gas phase substance that can barely be seen by human eye, while microscopically the mist fluid contains tiny droplets in aqueous phase.

Commercially available high-throughput humidifiers do not possess the mist throughput and delivery strategies discussed herein. Further, available humidifiers would not be well suited for use in the production of mist having a high quantity of smaller micron and sub-micron droplets. Thus, currently available humidifier technology would not be contemplated for use in a variety of applications such as fire suppression or sterilization in which a pseudo gas-phase substance delivered at high throughput levels would be desirable.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention as defined by the claims.

We claim:

1. A method for producing a high throughput aerosol or mist comprising the steps of:

a. providing a substance for generation of smaller particles or droplets thereof;

b. generating smaller particles or droplets from said substance;

c. directing a helical flow of a carrier medium with respect to the smaller particles or droplets;

d. creating an aerosol or mist including the combination of carrier medium and the smaller particles or droplets; and    e. delivering the aerosol or mist such that the aerosol or mist behaves as a pseudogas.

2. A method for producing a high throughput aerosol or mist as in claim 1 in which said step of delivering the aerosol or mist includes the additional step of deflecting said aerosol or mist upwards and providing a tube centrally situated with respect to said helical flow of the carrier medium such that said aerosol or mist will discharge through said tube.

3. A device for generating a mist comprising:

a container;

a high frequency wave generating device;

a reservoir for holding fluid in communication with the high frequency wave generating device for producing a fountain column having a central portion and a peripheral portion within the container;

a helical flow provider situated with respect to the container so as to provide a helical flow of a carrier medium about the peripheral portion of the fountain column and without significantly disturbing the central portion of the fountain column such as would create a greater portion of larger droplets within the mist; and a mist outlet situated on the container for mist emission.

4. A device for generating a mist as in claim 3 in which the high frequency wave generating device is a piezoelectric transducer or laser beam.

5. A device for generating a mist as in claim 3 in which a portion of the container on which the helical flow provider and the mist outlet are situated is cylindrical.

6. A device for generating a mist as in claim 3 in which the mist outlet is tangentially situated to the fountain column.

7. A device for generating a mist as in claim 3 in which said fountain column includes an upper portion and a lower portion and the mist outlet is tangentially situated to the upper portion of the fountain column.

8. A device for generating a mist as in claim 3 in which said mist outlet includes a tube centrally situated on the container such that a first extension of the tube extends into the container to a point below the helical flow provider and a second extension of the tube extends outward from the container.

9. A device for generating a mist as in claim 3 in which said container includes a conical portion having an upwardly oriented conically converging diameter and the mist outlet is connected to the conical portion.

10. A device for generating a mist comprising:
   a container having multiple mist outlets situated on the container for mist emission;
   a high frequency wave generating device;
   a reservoir for holding a fluid in communication with the high frequency wave generating device for producing a fountain column within the container;
   a helical flow provider situated with respect to the container so as to provide a helical flow of a carrier medium; and
   a mist outlet situated on the container for mist emission.

11. A device for generating a mist as in claim 3 in which said helical flow provider includes a carrier medium inlet tangentially situated to the fountain column.

12. A device for generating a mist comprising:
   a container;
   a high frequency wave generating device;
   a reservoir for holding fluid in communication with the high frequency wave generating device for producing a fountain column within the container;
   a helical flow provider situated with respect to the container so as to provide a helical flow of a carrier medium and having multiple carrier medium inlets on the container tangentially situated to the fountain column; and
a mist outlet situated on the container for mist emission.

13. A device for generating a mist as in claim 3 in which said helical flow provider includes a separate helical or swirl flow generating device attached to said container so as to communicate said helical flow of the carrier medium to the container.

14. A device for generating a mist as in claim 3 in which said fountain column includes an upper portion and a lower portion and the carrier medium inlet is tangentially situated to the upper portion of the fountain column and the mist outlet is tangentially situated to the lower portion of the fountain column and situated above the reservoir.

15. A device for generating a mist as in claim 3 in which said high frequency wave generating device is comprised of an array of piezoelectric transducers arranged in combination.

16. A device for generating a mist as in claim 3 in which said high frequency wave generating device is comprised of several annularly arranged transducers and said container includes an annular chamber for causing an annular flow of air within the container.

17. A device for generating a mist comprising:
   a container;
   a high frequency wave generating device;
   a reservoir for holding fluid in communication with the high frequency wave generating device for producing a fountain column having a central portion and an exterior portion within the container;
   a carrier medium inlet situated with respect to the fountain column for directing a flow of carrier medium about the exterior portion of the fountain column without significantly disturbing the central portion of the fountain column; and
   a mist outlet situated on the container for mist emission.

18. A device for generating a mist as in claim 17 in which said mist outlet includes a tube centrally situated on the container such that a first extension of the tube extends into the container to a point below the carrier medium inlet and a second extension of the tube extends outward from the container.

19. A device for generating a mist as in claim 17 in which said high frequency wave generating device is comprised of several annularly arranged transducers and the flow of carrier medium is directed in a helical flow about the fountain column.

20. A method for producing a mist comprising the steps of:
   a. providing a liquid for atomization;
   b. producing a fountain column having a central portion and a circumferential outer portion by atomizing the liquid;
   c. directing a carrier medium about the circumferential portion of the fountain column so as not to significantly disrupt the central portion of the fountain column;
   d. mixing mist droplets from the fountain column into the carrier medium; and
   e. discharging the mist.

21. A method for producing a mist as in claim 20 in which the step of directing the carrier medium with the respect to the fountain column so as not to significantly disrupt the central portion of the fountain column includes directing the carrier medium tangentially with respect to the fountain column.

22. A method for producing a mist comprising the steps of:
   a. providing a liquid for atomization;
   b. producing a fountain column having a central portion by atomizing the liquid;
   c. directing a carrier medium with respect to the fountain column so as not to significantly disrupt the central portion of the fountain column including creating a helical flow of the carrier medium within a cylindrical container having an outer wall such that the velocity of the carrier medium flow near the outer wall of the cylindrical container is greater than the velocity of carrier medium flow near the central portion of the fountain column;
   d. mixing mist droplets from the fountain column into the carrier medium; and
   e. discharging the mist.

23. A method for producing a mist as in claim 20 in which the step of mixing mist droplets into the carrier medium includes entraining the mist droplets into the carrier medium.

24. A method for producing a mist as in claim 20 in which the discharged mist is comprised of a substantial quantity of the mist droplets that are less than 10 micron in diameter.

25. A method of producing a mist as in claim 20 in which the discharged mist is comprised of a substantial quantity of the mist droplets that are less than one micron in diameter.

26. A method of producing a mist as in claim 20 in which said step of producing a fountain column having a central portion is accomplished at ambient pressure using at least one high frequency wave generating device.

27. A method of producing a mist as in claim 26 in which each said high frequency wave generating device is a piezoelectric transducer.

28. A method of producing a mist as in claim 26 including the step of scaling throughput of discharging mist by varying frequency of each said high frequency wave generating device.

29. A method of producing a mist as in claim 26 in which each said high frequency wave generating device includes an oscillator surface area and includes the step of scaling throughput of discharging mist by varying oscillator surface area of each said high frequency wave generating device.

30. A method of producing a mist as in claim 26 including the step of scaling throughput of discharging mist by using a multiple channel system of high frequency wave generating devices.

31. A method of producing a mist as in claim 20 in which said step of discharging the mist includes directing the mist through an outlet situated tangentially with respect to the fountain column.

32. A method of producing a mist as in claim 20 in which said step of discharging the mist includes directing the mist through an outlet situated above the fountain column.

33. A method of producing a mist as in claim 22 in which said step of discharging the mist includes directing the mist through a tube centrally situated on the cylindrical container such that a first portion of the tube extends inward into the cylindrical container and a second portion of the tube extends outward from the container.

34. A method of producing a mist as in claim 20 in which said step of discharging the mist includes directing the mist through a member having a conically converging diameter and an outlet connected to the member.

35. A method for producing a mist comprising the steps of:
   a. providing a liquid for atomization;
   b. producing a fountain column having a central portion by atomizing the liquid;
   c. directing a carrier medium tangentially with respect to the fountain column by multiple inlets of carrier medium tangentially situated to the fountain column so as not to significantly disrupt the central portion of the fountain column;
   d. mixing mist droplets from the fountain column into the carrier medium; and
   e. discharging the mist.

36. A method for producing a mist comprising the steps of:
   a. providing a liquid for atomization;
   b. producing a fountain column having a central portion by atomizing the liquid within a container having an upper portion and a lower portion;
   c. directing a carrier medium tangentially with respect to the fountain column by an inlet of carrier medium tangentially situated to the fountain column on the upper portion of the container so as not to significantly disrupt the central portion of the fountain column;
   d. mixing mist droplets from the fountain column into the carrier medium; and
   e. discharging the mist by directing the mist through an outlet tangentially situated to the fountain column on the lower portion of the container.

37. A method for producing a mist comprising the steps of:
   a. providing a liquid for atomization;
   b. adding a chemical additive to the liquid for atomization to decrease the surface tension of the liquid;
   c. producing a fountain column having a central portion by atomizing the liquid;
   d. directing a carrier medium about the circumferential portion of the fountain column so as not to significantly disrupt the central portion of the fountain column;
   e. mixing mist droplets from the fountain column into the carrier medium; and
   f. discharging the mist.

38. A method of producing a mist comprising the steps of:
   a. providing a liquid for atomization;
   b. producing a fountain column having a central portion by atomizing the liquid;
   c. directing a carrier medium with respect to the fountain column so as not to significantly disrupt the central portion of the fountain column;
   d. mixing mist droplets from the fountain column into the carrier medium; and
   e. discharging the mist at a predetermined throughput of at least one liter per minute.

39. A method of producing a mist comprising the steps of:
   a. providing a liquid for atomization;
   b. producing a fountain column having a central portion by atomizing the liquid;
   c. directing a carrier medium with respect to the fountain column so as not to signficantly disrupt the central portion of the fountain column;
   d. mixing mist droplets from the fountain column into the carrier medium; and
   e. discharging the mist, whereby the mist behaves as a pseudo-gas after discharging and maintains liquid droplet properties.

40. A device for producing a mist comprising:
   a first mist generator including a container, a high frequency wave generating device, a power supply attached to the high frequency wave generating device, a reservoir for holding fluid in communication with the high frequency wave generating device for producing a fountain column within the container, a carrier medium inlet tangentially situated to the fountain column, and a mist outlet situated on the container for mist emission;
   at least one additional mist generator including a container, a high frequency wave generating device, a power supply attached to the high frequency wave generating device, a reservoir for holding fluid in communication with the high frequency wave generating device for producing a fountain column within the container, a carrier medium inlet tangentially situated to the fountain column, and a mist outlet situated on the container for mist emission; and
   a conduit connecting said first mist generator and said at least one additional mist generator in series to provide successive chambers which receive mist flow.

* * * * *